United States Patent
Ito et al.

(10) Patent No.: US 10,762,384 B2
(45) Date of Patent: Sep. 1, 2020

(54) RADIATION IMAGE CAPTURE SYSTEM AND BODY SYSTEM ESTIMATION METHOD WITH SCATTER REDUCTION

(71) Applicant: Konica Minolta, Inc., Chiyoda-ku, Tokyo (JP)

(72) Inventors: Ryohei Ito, Hino (JP); Tatsuya Takagi, Mitaka (JP); Keita Yoshida, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 511 days.

(21) Appl. No.: 15/099,944

(22) Filed: Apr. 15, 2016

(65) Prior Publication Data
US 2016/0302752 A1    Oct. 20, 2016

(30) Foreign Application Priority Data
Apr. 15, 2015    (JP) ................................. 2015-083255

(51) Int. Cl.
*G06K 9/62* (2006.01)
*A61B 6/00* (2006.01)
(Continued)

(52) U.S. Cl.
CPC .......... *G06K 9/6212* (2013.01); *A61B 6/4283* (2013.01); *A61B 6/5211* (2013.01);
(Continued)

(58) Field of Classification Search
CPC .......... A61B 6/00; A61B 6/42; A61B 6/4283; A61B 6/4291; A61B 6/52; A61B 6/5211;
(Continued)

(56) References Cited

U.S. PATENT DOCUMENTS

2007/0268997 A1 * 11/2007 Zhu ....................... A61B 6/5282
                                                              378/7
2009/0147911 A1 * 6/2009 Joosten ..................... A61B 6/06
                                                              378/7
(Continued)

FOREIGN PATENT DOCUMENTS

JP        S61133847 A    6/1986
JP        07178076 A     7/1995
(Continued)

OTHER PUBLICATIONS

JPO Notification of Reasons for Refusal corresponding to JP Application No. 2015-083255; dated Oct. 30, 2018.
(Continued)

*Primary Examiner* — Anastasia Midkiff
(74) *Attorney, Agent, or Firm* — Cantor Colburn LLP

(57) ABSTRACT

A radiation image capturing system includes a radiation image capturing apparatus, an irradiation apparatus and an image processing apparatus. The image processing apparatus generates a first radiation image of a subject based on a signal value generated by the radiation image capturing apparatus with no grid attached irradiated by the irradiation apparatus; performs a low-pass filter process on a pixel value of the first radiation image using a scattering kernel, thereby generating a low frequency image; estimates a body thickness of the subject based on the signal value; estimates a scattered ray content rate based on the body thickness; calculates a scattered ray component in the first radiation image based on the low frequency image and the scattered ray content rate; and subtracts the scattered ray component from the first radiation image, thereby generating a second radiation image.

9 Claims, 14 Drawing Sheets

(51) Int. Cl.
| | |
|---|---|
| *G06T 5/50* | (2006.01) |
| *G06T 7/00* | (2017.01) |
| *G06T 5/40* | (2006.01) |
| *G06K 9/20* | (2006.01) |
| *G06K 9/60* | (2006.01) |
| *G06K 9/36* | (2006.01) |
| *G06K 9/46* | (2006.01) |
| *H04N 5/32* | (2006.01) |
| *G06K 9/78* | (2006.01) |
| *G06K 9/80* | (2006.01) |

(52) U.S. Cl.
CPC .......... *A61B 6/5235* (2013.01); *A61B 6/5282* (2013.01); *G06K 9/2054* (2013.01); *G06K 9/36* (2013.01); *G06K 9/4642* (2013.01); *G06K 9/60* (2013.01); *G06T 5/40* (2013.01); *G06T 5/50* (2013.01); *G06T 7/0014* (2013.01); *A61B 6/4291* (2013.01); *G06K 9/78* (2013.01); *G06K 9/80* (2013.01); *G06T 2207/20024* (2013.01); *G06T 2207/20224* (2013.01); *H04N 5/3205* (2013.01)

(58) Field of Classification Search
CPC ... A61B 6/5217; A61B 6/5229; A61B 6/5235; A61B 6/5258; A61B 6/5282; A61B 6/5294; A61B 2576/00; A61B 2576/02; G06T 5/00; G06T 5/007; G06T 5/009; G06T 5/20; G06T 5/40; G06T 5/50; G06T 7/00; G06T 7/0002; G06T 7/0012; G06T 7/0014; G06T 7/10; G06T 7/50; G06T 7/60; G06T 2207/10; G06T 2207/10116; G06T 2207/20; G06T 2207/20004; G06T 2207/20008; G06T 2207/20024; G06T 2207/20212; G06T 2207/20224; G06T 2207/30; G06T 2207/30004; G06K 9/00; G06K 9/20; G06K 9/2054; G06K 9/36; G06K 9/46; G06K 9/4604; G06K 9/4609; G06K 9/4642; G06K 9/4647; G06K 9/52; G06K 9/522; G06K 9/54; G06K 9/60; G06K 9/62; G06K 9/6201; G06K 9/6202; G06K 9/6212; G06K 9/6267; G06K 9/6268; G06K 9/627; G06K 9/6276; G06K 9/74; G06K 9/741; G06K 9/743; G06K 9/78; G06K 9/80; G06K 2209/00; G06K 2209/05; G06K 2209/40; H04N 5/30; H04N 5/32; H04N 5/3205; H04N 2201/00; H04N 2201/0077; H04N 2201/0079; G01N 2223/00; G01N 2223/40; G01N 2223/401; G01N 2223/408; G01N 2223/42; G01N 2223/421

See application file for complete search history.

(56) References Cited

U.S. PATENT DOCUMENTS

| | | | |
|---|---|---|---|
| 2012/0148156 | A1 | 6/2012 | Sehnert |
| 2014/0146935 | A1* | 5/2014 | Goldammer ......... A61B 6/4035 378/7 |
| 2015/0251018 | A1* | 9/2015 | Tajima .................... G06T 5/002 378/28 |
| 2016/0081648 | A1* | 3/2016 | Tajima ................. A61B 6/5282 378/165 |
| 2016/0086328 | A1* | 3/2016 | Enomoto ................ G06T 11/60 382/132 |
| 2016/0089094 | A1* | 3/2016 | Kawamura ............ A61B 6/461 378/62 |
| 2017/0055933 | A1* | 3/2017 | Kawamura .......... A61B 6/5282 |

FOREIGN PATENT DOCUMENTS

| | | |
|---|---|---|
| JP | 2014207958 A | 11/2014 |
| JP | 2015043959 A | 3/2015 |
| JP | 2015043960 A | 3/2015 |

OTHER PUBLICATIONS

JPO Notification of Reasons for Refusal corresponding to Application No. 2015-083255; dated Apr. 2, 2019.

* cited by examiner

RADIATION IMAGE CAPTURE SYSTEM AND BODY SYSTEM ESTIMATION METHOD WITH SCATTER REDUCTION

CROSS REFERENCE TO RELATED APPLICATIONS

The present invention claims priority under 35 U.S.C. § 119 to Japanese Application No. 2015-083255 filed Apr. 15, 2015, the entire content of which is incorporated herein by reference.

FIELD OF THE INVENTION

The present invention relates to a radiation image capturing system and a body thickness estimation method.

DESCRIPTION OF THE RELATED ART

There have been developed various radiation image capturing apparatuses which generate electric charge at radiation detection elements according to the dose of radiation such as X-ray with which the radiation detection elements are irradiated, and read out the generated electric charge as image data. This type of radiation image capturing apparatus is known as FPD (Flat Panel Detector) and conventionally integrated with a support, called the specialized-type (also called the fixed-type, etc.), but recently has been developed to be portable, called the portable-type (also called the cassette-type, etc.), formed such that radiation detection elements and so forth are housed in a housing, and it is now in practical use.

When radiation image capturing is performed by this type of radiation image capturing apparatus, in order to prevent scattered rays, which are rays scattered by a subject, from entering the radiation image capturing apparatus and accordingly prevent quality of captured radiation images from decreasing, it is often performed by a radiation image capturing apparatus 1 with a grid Gr attached onto a radiation incident face R side of a housing 2 as shown in FIG. 15.

As described above, nowadays, there are portable radiation image capturing apparatuses. Hence, radiation image capturing can be performed by carrying a portable radiation image capturing apparatus and/or a portable irradiation apparatus into a hospital ward, patient's home or the like. However, in this situation, the grid Gr and an X-ray tubular lamp of the irradiation apparatus are often not accurately aligned.

As it is well known, when the grid Gr and the X-ray tubular lamp are not accurately aligned, quality of captured radiation images decreases. Therefore, in the above situation, the grid Gr is often not used. However, when no grid Gr is attached to the radiation image capturing apparatus, scattered rays decrease contrast of captured radiation images and/or increase noise thereon. This decreases quality of captured radiation images.

Then, there are described, for example, in Japanese Patent Application Publication Nos. S61-133847, 2014-207958 and 2015-43959 technologies of image processing on radiation images, by which even if radiation image capturing is performed by a radiation image capturing apparatus with no grid Gr attached, scattered rays can be removed to the same level as that performed by the radiation image capturing apparatus with the grid Gr attached.

By the way, the content rate of scattered rays ("scattered ray content rate(s)" hereinafter) in a captured radiation image varies at least according to the body thickness of a subject (patient). Hence, in the conventional technologies described in Japanese Patent Application Publication Nos. S61-133847, 2014-207958 and 2015-43959, the body thickness of a subject is estimated by measurement using a sensor or the like or by approximation using a cubic, circular cylindrical or elliptic cylindrical model, for example.

The inventors of this application have further studied these estimation methods of the body thickness and found a method which can accurately estimate the body thickness of a subject by image analysis of a captured radiation image, without use of a sensor or the like.

BRIEF SUMMARY OF THE INVENTION

The present invention has been made in view of the above points, and objects of the present invention include providing: a body thickness estimation method which can accurately estimate the body thickness of a subject by image analysis of a captured radiation image, without use of a sensor or the like; and a radiation image capturing system which can accurately estimate the body thickness of a subject by image analysis of a captured radiation image, without use of a sensor or the like, and obtain a radiation image with a scattered ray component(s) properly removed, based on the accurately estimated body thickness.

In order to achieve at least one of the objects, according to a first aspect of the present invention, there is provided a radiation image capturing system including: a radiation image capturing apparatus including: a plurality of radiation detection elements which are arranged two-dimensionally and generate electric charge according to a dose of radiation with which the radiation detection elements are irradiated; and a control unit which converts the electric charge generated in each of the radiation detection elements into a signal value; an irradiation apparatus which, via a subject, irradiates the radiation image capturing apparatus with the radiation; and an image processing apparatus which generates a first radiation image based on the signal value, which corresponds to the electric charge generated in each of the radiation detection elements, wherein the image processing apparatus: generates the first radiation image based on the signal value generated by the radiation image capturing apparatus with no grid attached irradiated by the irradiation apparatus; performs a low-pass filter process on a pixel value of the first radiation image using a scattering kernel, thereby generating a low frequency image; estimates a body thickness of the subject based on the signal value; estimates a scattered ray content rate based on the body thickness; calculates a scattered ray component in the first radiation image based on the low frequency image and the scattered ray content rate; and subtracts the scattered ray component from the first radiation image, thereby generating a second radiation image with the scattered ray component removed.

According to a second aspect of the present invention, there is provided a body thickness estimation method including: estimating a body thickness of a subject based on a signal value generated by an irradiated radiation image capturing apparatus with no grid attached, the method further including: setting a region of interest at one part or multiple parts in a radiation image captured by the radiation image capturing apparatus; throwing the signal value for each pixel belonging to the region of interest into a histogram; and calculating a characteristic amount from the histogram, wherein the body thickness is estimated based on the characteristic amount.

According to a third aspect of the present invention, there is provided a body thickness estimation method including:

estimating a body thickness of a subject based on a pixel value of a radiation image captured by a radiation image capturing apparatus with no grid attached, wherein the body thickness is estimated based on shape information on the subject captured in the radiation image.

BRIEF DESCRIPTION OF THE SEVERAL VIEWS OF THE DRAWING

The present invention is fully understood from the detailed description given hereinafter and the accompanying drawings, which are given by way of illustration only and thus are not intended to limit the present invention, wherein.

DETAILED DESCRIPTION OF THE INVENTION

Hereinafter, embodiments of a radiation image capturing system of the present invention are described with reference to the drawings. A body thickness estimation method of the present invention is described in the description of the radiation image capturing system of the present invention.

Hereinafter, a radiation image capturing apparatus constituted of a sensor panel housed in a housing, thereby being portable, namely, a portable radiation image capturing apparatus, is described. However, the present invention is also applicable to a conventional radiation image capturing apparatus integrated with a support or the like installed in a radiography room. The present invention is also applicable to a portable radiation image capturing apparatus fitted in a Bucky device in a radiography room so as to perform radiation image capturing.

[Radiation Image Capturing Apparatus]

Figure 1:
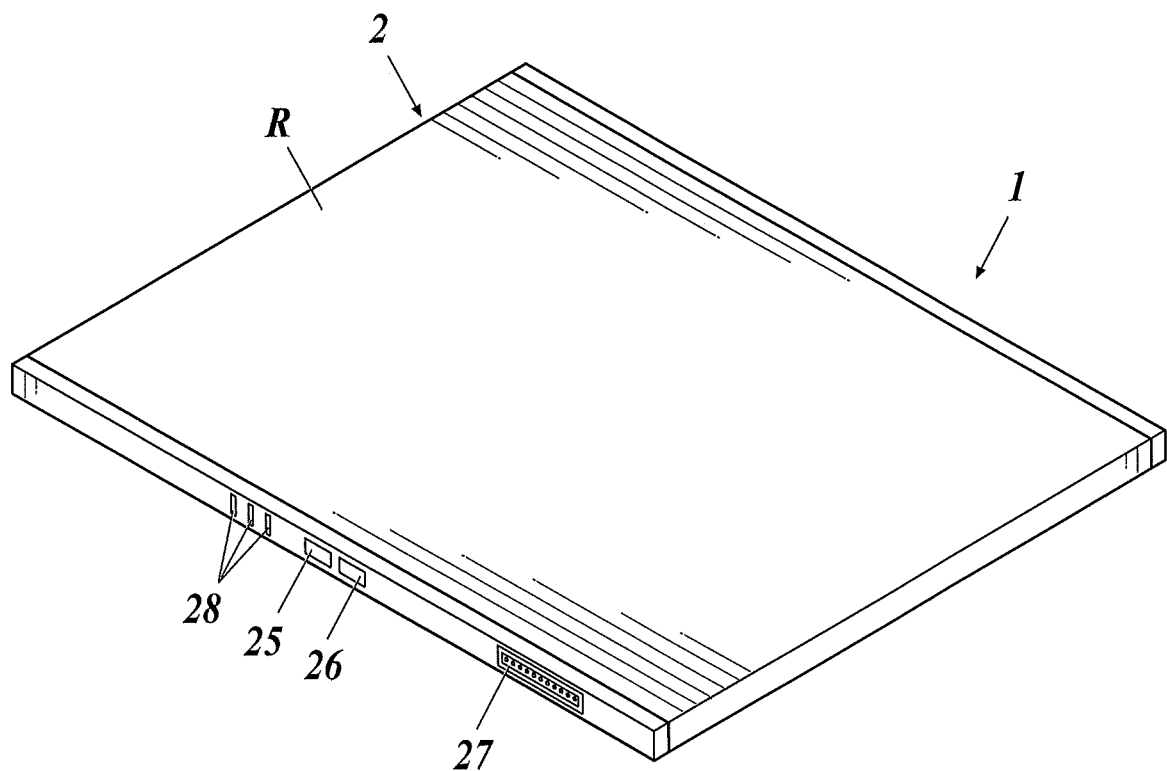
FIG. 1 is a perspective view showing external appearance of a radiation image capturing apparatus according to embodiments of the present invention.

First, a radiation image capturing apparatus 1 used in a radiation image capturing system according to embodiments of the present invention is described. FIG. 1 is a perspective view showing external appearance of the radiation image capturing apparatus 1.

In the embodiments, the radiation image capturing apparatus 1 is configured such that radiation detection elements 7, described below, and so forth are housed in a housing 2. One lateral face of the housing 2 is provided with a power switch 25, a switch 26, a connector 27, indicators 28 and so forth. In addition, although not shown, for example, the opposite lateral face of the housing 2 is provided with an antenna 29 (shown in FIG. 2 described below) for wireless communication with outside. For wired communication with outside, a not-shown cable is connected to the connector 27.

Figure 2:
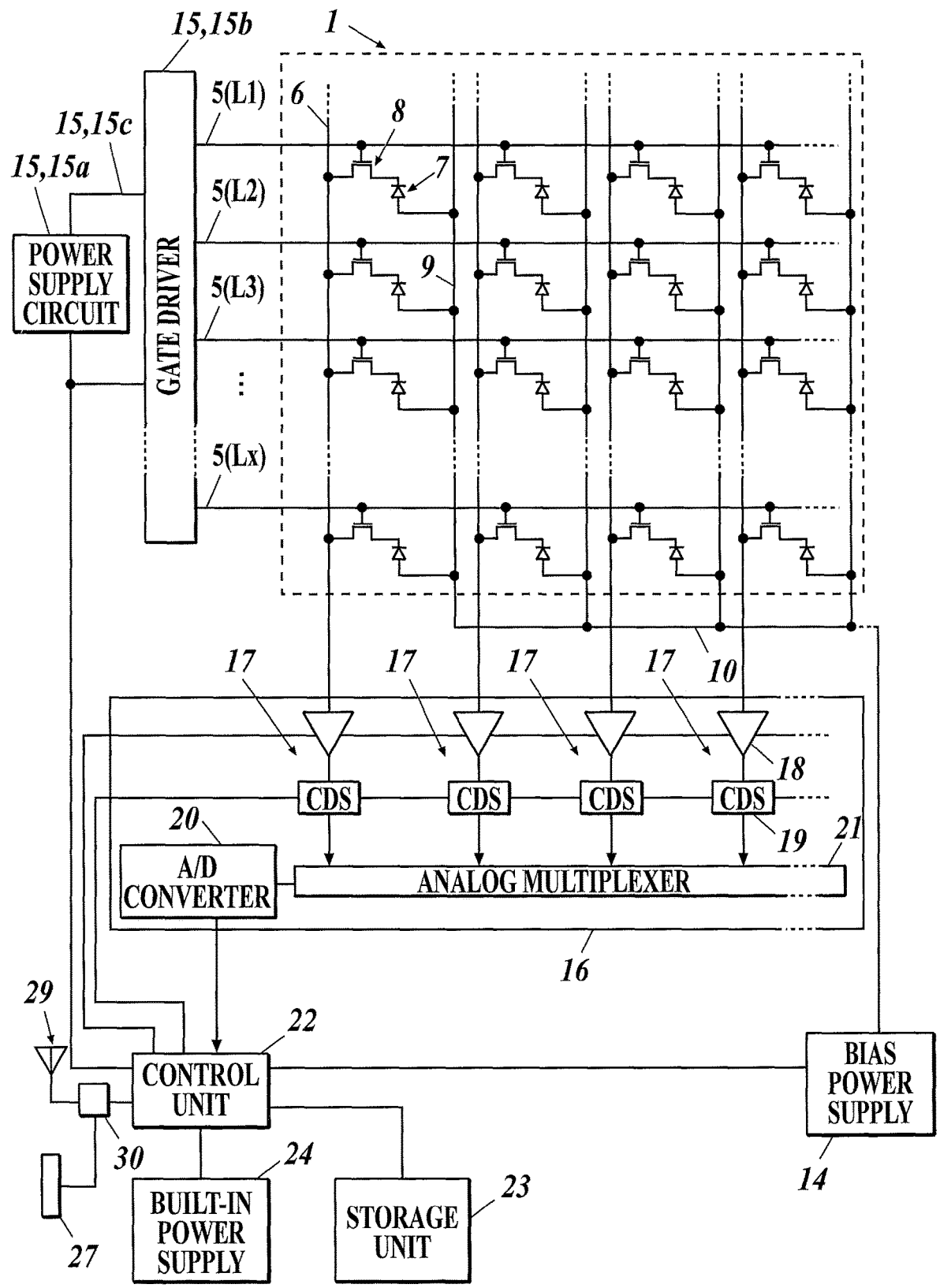
FIG. 2 is a block diagram showing an equivalent circuit of the radiation image capturing apparatus.

FIG. 2 is a block diagram showing an equivalent circuit of the radiation image capturing apparatus 1. As shown in FIG. 2, in the radiation image capturing apparatus 1, radiation detection elements 7 are arranged two-dimensionally (i.e., in a matrix) on a not-shown sensor substrate. The radiation detection elements 7 generate electric charge according to the dose of radiation with which the radiation detection elements 7 are irradiated. The radiation detection elements 7 are connected to bias lines 9, and the bias lines 9 are connected to a tie line 10. The tie line 10 is connected to a bias power supply 14, and reverse bias voltage is applied to the radiation detection elements 7 from the bias power supply 14 via the bias lines 9 and so forth.

The radiation detection elements 7 are connected to thin film transistors (TFTs) 8, which are switch elements, and the TFTs 8 are connected to signal lines 6. In a scan driving unit 15, ON voltage and OFF voltage supplied from a power supply circuit 15a via wiring 15c are switched by a gate driver 15b so as to be applied to lines L1 to Lx of scan lines 5. When ON voltage is applied to the TFTs 8 via the scan lines 5, the TFTs 8 are set to the ON state and release electric charge accumulated in the radiation detection elements 7 to the signal lines 6. When OFF voltage is applied to the TFTs 8 via the scan lines 5, the TFTs 8 are set to the OFF state, and break electrical continuity of the radiation detection elements 7 and the signal lines 6 and accumulate electric charge in the radiation detection elements 7, the electric charge being generated thereat.

In a readout IC 16, readout circuits 17 are provided, and the readout circuits 17 are connected to their respective signal lines 6. In an image data D readout process, when ON voltage is applied to the TFTs 8 from the gate driver 15b of the scan driving unit 15 via the scan lines 5 under the control of a control unit 22, described below, the TFTs 8 are set to the ON state and release electric charge from the radiation detection elements 7 to the signal lines 6.

The released electric charge flows into the readout circuits 17 via the signal lines 6, and the amplifier circuits 18 output voltage values according to the amounts of the electric charge having flowed thereinto. Then, correlated double sampling circuits 19 ("CDSs" in FIG. 2) read and output to the downstream the voltage values output from the amplifier circuits 18 as analog value image data D. The output image data D are sequentially sent to an A/D converter 20 via an analog multiplexer 21. The A/D converter 20 sequentially converts the received image data D into digital value image data D and outputs the digital value image data D to a storage unit 23 so as to sequentially store the digital value image data D therein. The control unit 22 thus performs the image data D readout process to read out electric charge from the radiation detection elements 7 as image data D.

The control unit 22 is constituted of, for example, a computer or an FPGA (Field Programmable Gate Array). The computer includes a CPU, a ROM, a RAM and an input-output interface which are connected to a bus (all not shown). The control unit 22 may be constituted of a specialized control circuit. The control unit 22 is connected to the storage unit 23 constituted of, for example, an SRAM (Static RAM), an SDRAM (Synchronous DRAM) or an NAND flash memory.

The control unit 22 is connected to a communication unit 30 which communicates with outside using a wireless system or wired system via the antenna 29 or connector 27. The control unit 22 is also connected to a built-in power supply 24 such as a lithium-ion capacitor to supply a necessary amount of power to the functional parts, such as the scan driving unit 15, the readout circuits 17, the storage unit 23 and the bias power supply 14.

[Radiation Image Capturing System]

Next, a configuration example of a radiation image capturing system 50 according to the embodiments is briefly described. As described above, the radiation image capturing system 50 of the embodiments can use a radiation image capturing apparatus installed in a radiography room or a radiation image capturing apparatus fitted in a Bucky device in a radiography room so as to perform radiation image capturing. The radiation image capturing system 50 can also be configured on a nursing cart 51 as shown in FIG. 3 so as to perform radiation image capturing with a portable irradiation apparatus carried into a hospital ward or the like.

Figure 3:
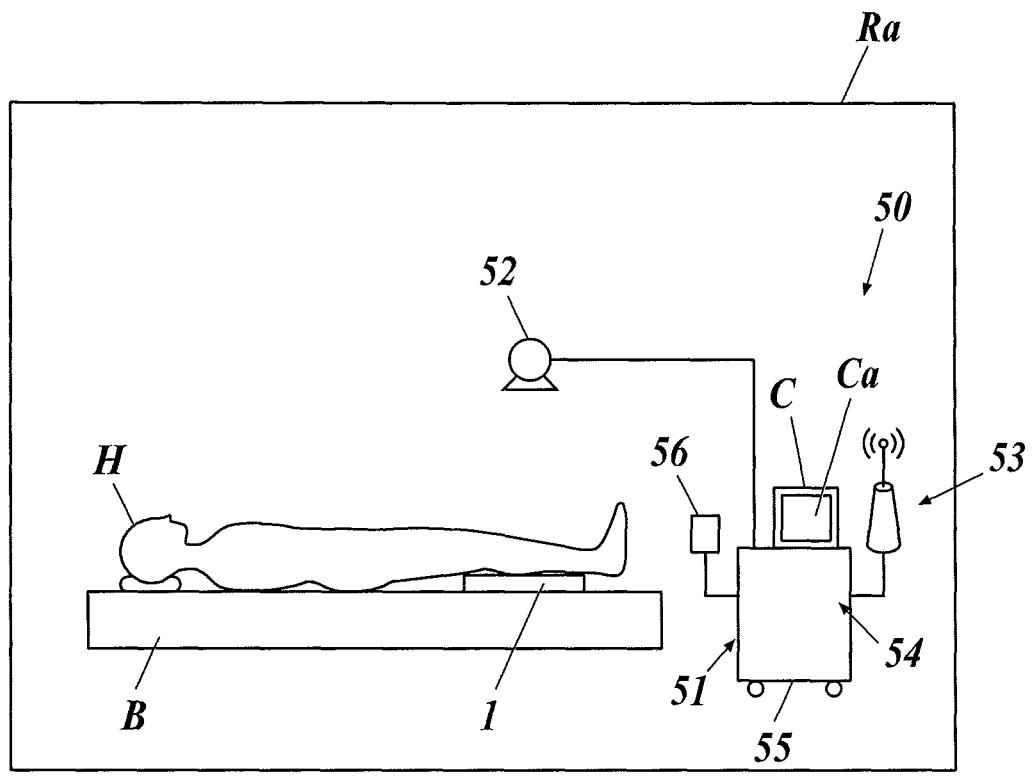
FIG. 3 shows a configuration example of a radiation image capturing system configured on a nursing cart.

In this case, as shown in FIG. 3, a portable irradiation apparatus 52 is carried into a hospital ward Ra or patient's home by being mounted on the nursing cart 51, for example. The irradiation apparatus 52 is configured to emit radiation in a desired direction, and hence can irradiate the radiation image capturing apparatus 1 via a subject H from an appropriate distance and an appropriate direction, the radiation image capturing apparatus 1 being inserted into between a bed B in the hospital ward Ra (or a bed or futon at patient's home) and the subject H or placed on the subject H.

In addition to the irradiation apparatus 52, there are mounted on the nursing cart 51, for example, a relay 54 provided with an access point 53, a generator 55 for the irradiation apparatus 52, an exposure switch 56 operated by an operator such as a radiologist to emit radiation from the irradiation apparatus 52, and a console C which controls operation of the radiation image capturing apparatus 1 to perform radiation image capturing.

The relay 54 relays wireless communication between (i) the radiation image capturing apparatus 1 and (ii) the console C, the irradiation apparatus 52 or the like via the access point 53. The relay 54 can also enable wired communication between the radiation image capturing apparatus 1 and the console C or the like by being connected to the radiation image capturing apparatus 1 via a not-shown cable or the like.

The console C is constituted of, for example, a computer including a CPU. The console C includes a display unit Ca constituted of a CRT (Cathode Ray Tube), an LCD (Liquid Crystal Display) or the like. Although not shown, the console C is connected to: an input unit such as a mouse or a key board; a storage unit constituted of an HDD (Hard Disk Drive) or the like; and so forth. In the embodiments, the console C is configured to function as an image processing apparatus, and hereinafter, when the console C functions as an image processing apparatus, it is described as an image processing apparatus C. However, it is possible to configure an image processing apparatus as a separate unit from the console C.

[Processes Performed by the Time Radiation Image is Generated]

Processes in radiation image capturing performed by the radiation image capturing apparatus 1, the console C and so forth by the time a radiation image P (a first radiation image) is generated by the console C are well known, and hence they are briefly described here.

When the radiation image capturing apparatus 1 is inserted into between the bed B and the subject H or placed on the subject H as described above, whereby positioning thereof is completed, and an operator such as a radiologist operates the exposure switch 56 for the irradiation apparatus 52, the generator 55 for the irradiation apparatus 52 sends a radiation emission start signal to the radiation image capturing apparatus 1.

Figure 4:
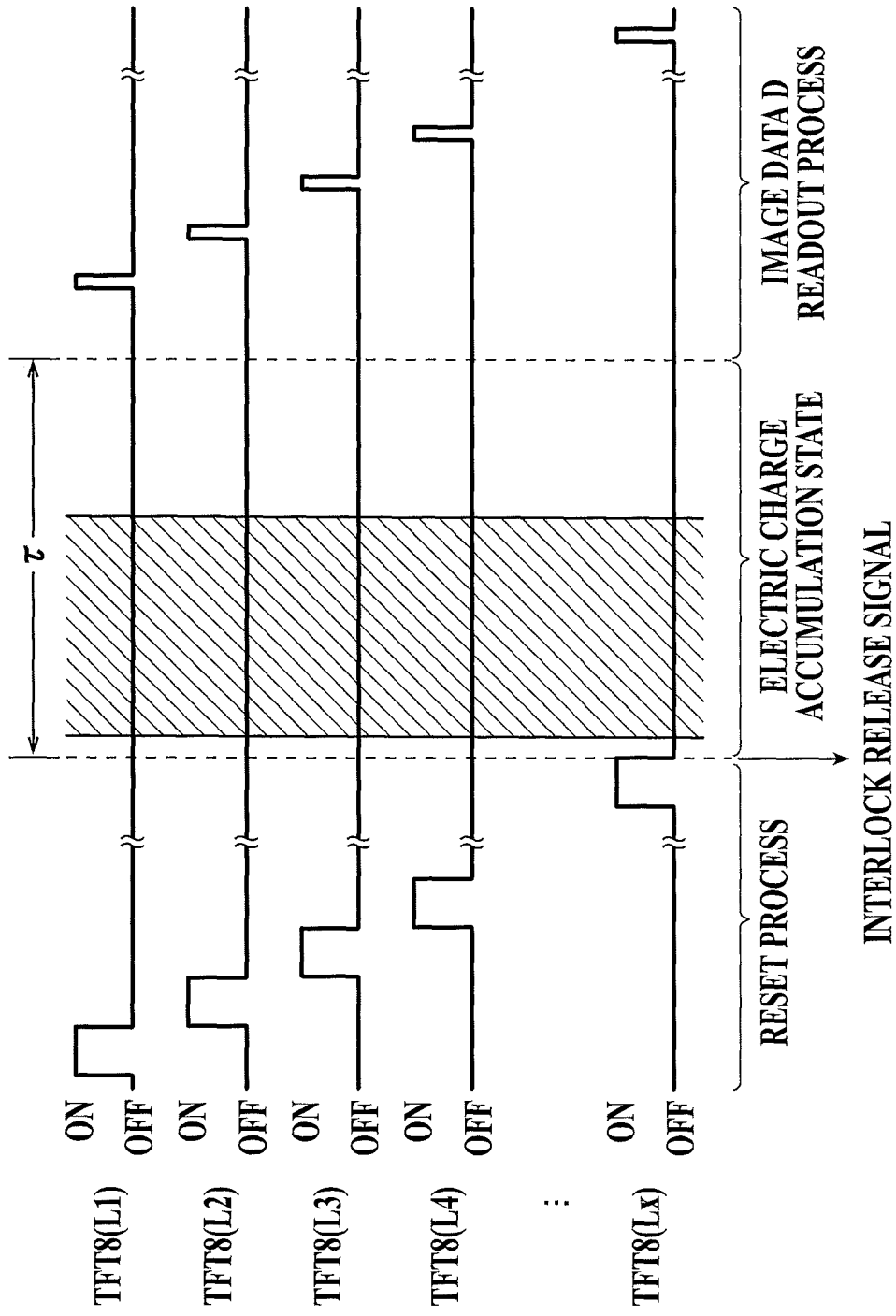
FIG. 4 is a timing chart for explaining timing to apply ON voltage to scan lines in a reset process, an electric charge accumulation state and an image data readout process of radiation detection elements.

When receives the radiation emission start signal, as shown in FIG. 4, the control unit 22 of the radiation image capturing apparatus 1 stops a reset process of the radiation detection elements 7 performed at the time, and controls the gate driver 15b (shown in FIG. 2) of the scan driving unit 15 to apply OFF voltage to the lines L1 to Lx of the scan lines 5 so as to set the TFTs 8 to the OFF state, thereby moving to an electric charge accumulation state.

At the time, the control unit 22 also sends an interlock release signal to the irradiation apparatus 52 side. When irradiation apparatus 52 receives the interlock release signal, the generator 55 for the irradiation apparatus 52 makes the irradiation apparatus 52 emit radiation. The hatched part in FIG. 4 represents a period of time that the irradiation apparatus 52 emits radiation.

Thus, radiation image capturing can be performed by the radiation image capturing apparatus 1 and the irradiation apparatus 52 side exchanging signals (i.e., being synchronized). Alternatively, radiation image capturing may be performed by the radiation image capturing apparatus 1 and the irradiation apparatus 52 side not exchanging signals. That is, the radiation image capturing apparatus 1 may be configured to detect start of radiation emission, i.e., irradiation, by itself, whereby radiation image capturing is performed asynchronously (i.e., uncooperatively). For details of such asynchronous image capturing, refer to, for example, Japanese Patent Application Publication No. 2009-219538 and International Patent Application Publication Nos. 2011/135917 and 2011/152093.

After keeping the electric charge accumulation state for a predetermined time τ as shown in FIG. 4, the control unit 22 of the radiation image capturing apparatus 1 controls the gate driver 15b to sequentially apply ON voltage to the lines L1 to Lx of the scan lines 5, thereby performing the image data D readout process of the radiation detection elements 7.

Figure 5:
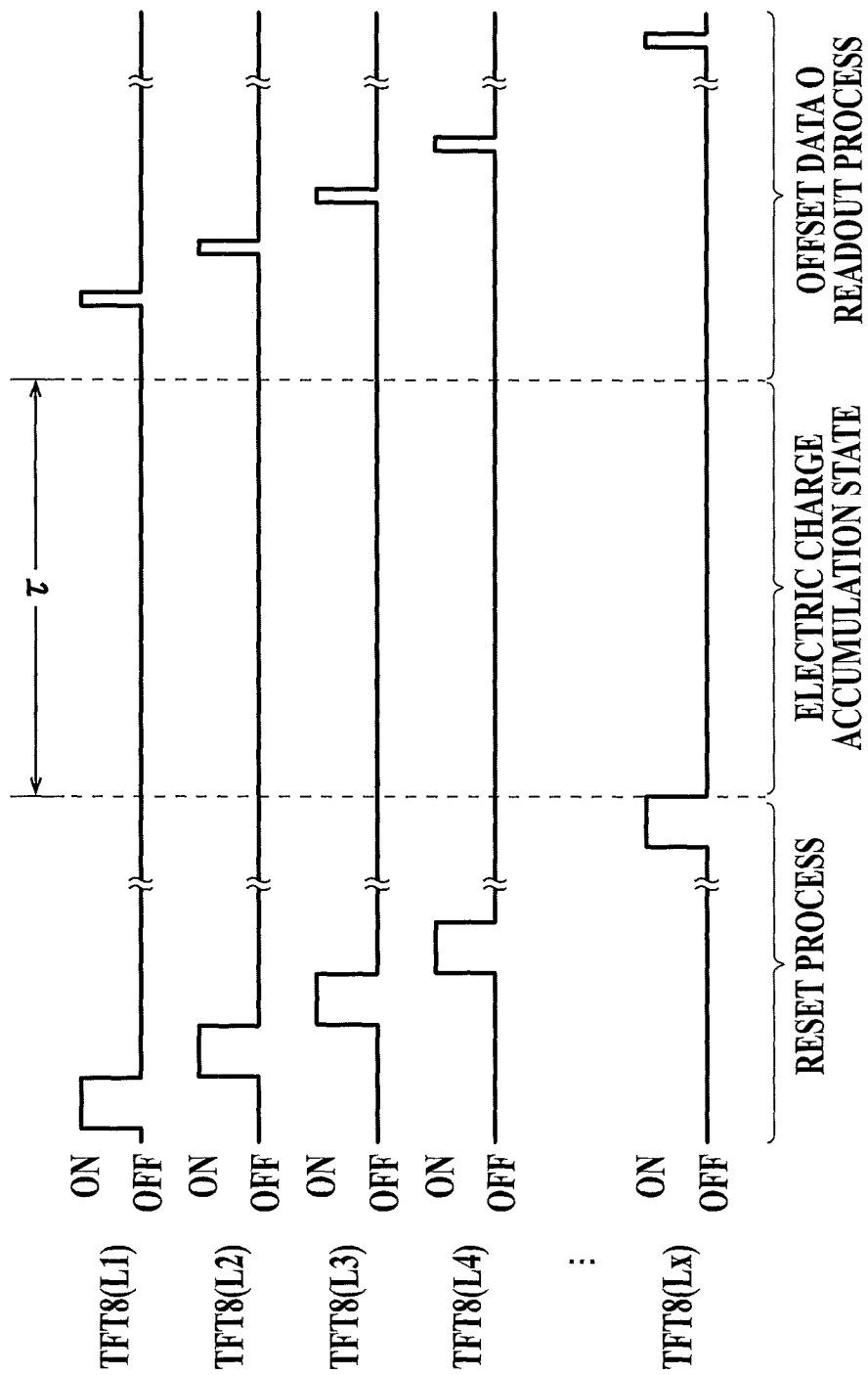
FIG. 5 is a timing chart for explaining timing to apply ON voltage to scan lines in a reset process, an electric charge accumulation state and an offset data readout process of the radiation detection elements.

Before or after radiation image capturing, the radiation image capturing apparatus 1 performs an offset data O readout process as shown in FIG. 5. That is, the radiation image capturing apparatus 1 repeats the sequence of the processes, which are performed before the image data D readout process in FIG. 4, thereby performing the reset process of the radiation detection elements 7 and keeping the electric charge accumulation state for the predetermined time τ without being irradiated, and then controls the gate driver 15b to sequentially apply ON voltage to the lines L1 to Lx of the scan lines 5, thereby reading out offset data O from the radiation detection elements 7 (i.e., performing the offset data O readout process), as with the image data D readout process.

Then, the radiation image capturing apparatus 1 transfers signal values Sp to the console C, namely, to the image processing apparatus C. The radiation image capturing apparatus 1 generates the signal values Sp by subtracting the offset data O from the image data D with respect to the respective radiation detection elements 7, namely, pixels, by the following formula (1). This generation of the signal values Sp based on the following formula (1) may be performed by the image processing apparatus C. In this case, the radiation image capturing apparatus 1 transfers the read-out image data D and offset data O to the image processing apparatus C.

$$Sp=D-O \quad (1)$$

The image processing apparatus C removes abnormal values from the signal values Sp transferred from the radiation image capturing apparatus 1, thereby correcting the signal values Sp to proper values (i.e., performing defect pixel correction), and then performs normalization to normalize the signal values Sp. In the normalization, the signal values Sp are converted, for example, such that the maximum value Spmax and the minimum value Spmin of the signal values Sp become predetermined maximum value SH and minimum value SL, respectively, thereby being normalized. More specifically, the image processing apparatus C converts the signal values Sp into normalized data Sp* by the following formula (2). The constants S and G in the formula (2) are determined such that the maximum value and the minimum value of the normalized data Sp* become SH and SL, respectively.

$$Sp^*=G \times Sp+S \quad (2)$$

The gradient G and the intercept S in the formula (2) represent a contrast value and a density correction value, respectively. The image processing apparatus C is configured to perform image processing using an LUT (Look Up Table) for the captured region (e.g., the front of the chest), such as gradation processing, on the normalized data Sp* so as to calculate pixel values Vp for respective pixels and thereby generate the radiation image P.

In the embodiments, as described above, the data generated by subtracting the offset data O from the image data D read out from the radiation detection elements 7 (i.e., pixels) of the radiation image capturing apparatus 1 is called the "signal values Sp" (corresponding to raw data), the data generated by normalizing the signal values Sp is called the "normalized data Sp*", and the final data generated by performing image processing using an LUT or the like on the normalized data Sp* is called the "pixel values Vp".

[Removal of Scattered Ray Components from Radiation Image Performed by Image Processing Apparatus]

Next, removal of scattered ray components from the radiation image performed by the image processing apparatus C of the radiation image capturing system 50 according to the embodiments is described. In the embodiments, the image processing apparatus C performs image processing similar to that described in the above-mentioned Japanese Patent Application Publication No. S61-133847, for example.

Figure 6:
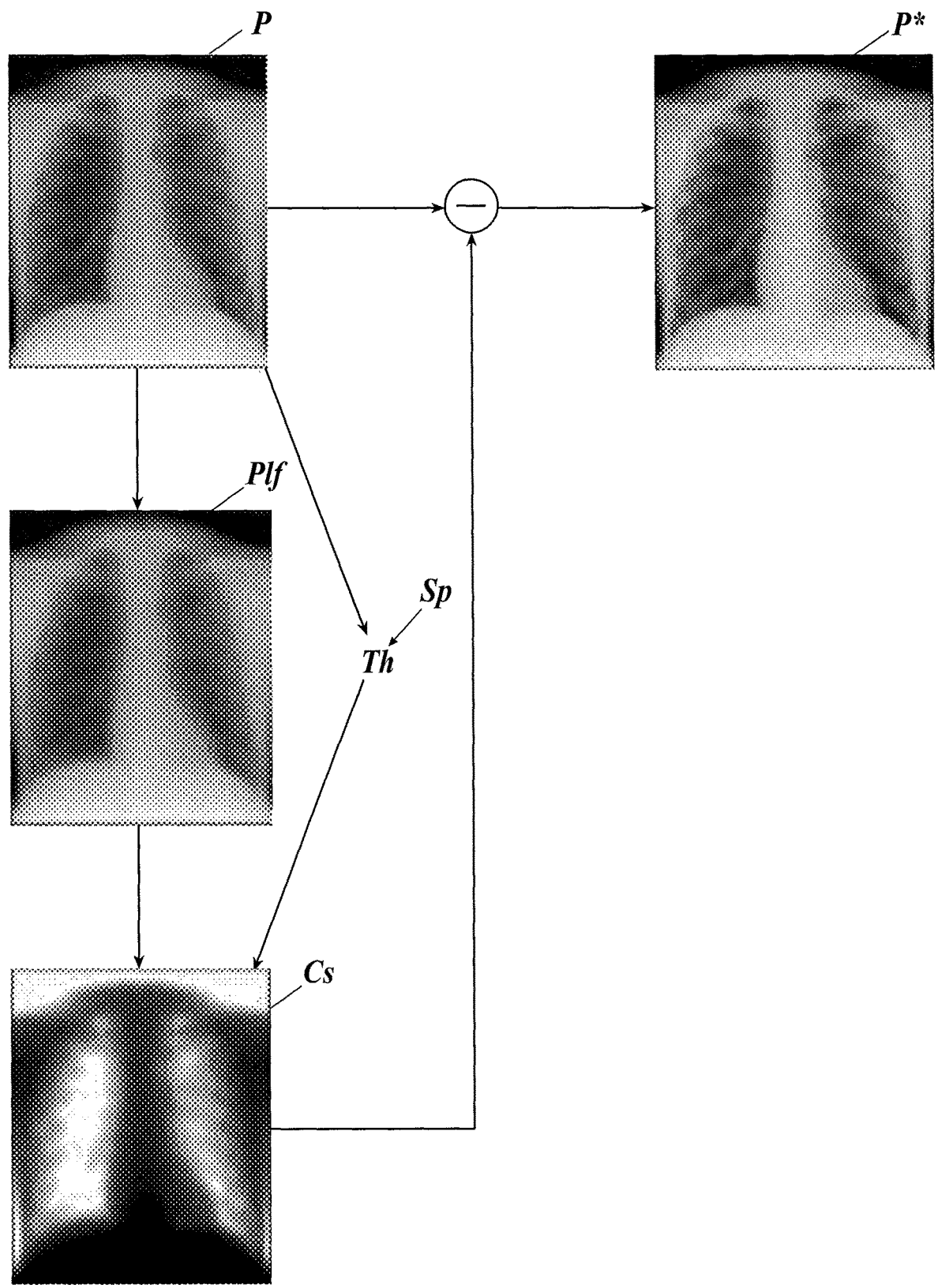
FIG. 6 is an illustration for explaining a procedure of removal of scattered ray components from a radiation image according to the embodiments.
Figure 15:
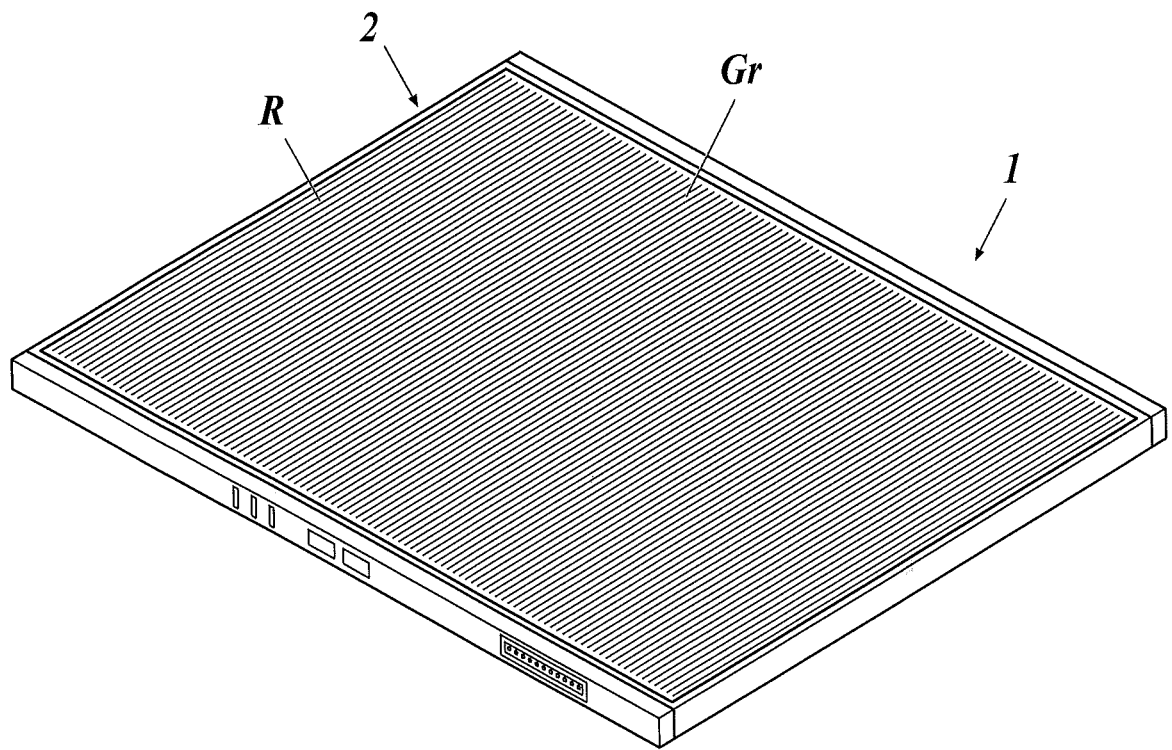
FIG. 15 shows an example of the grid attached to the radiation image capturing apparatus.

If radiation image capturing is performed by the radiation image capturing apparatus 1 with the grid Gr attached (shown in FIG. 15), the grid Gr is reflected in the radiation image P as a low frequency component. Hence, in the embodiments, the image processing apparatus C generates, as described above, the radiation image P based on the signal values Sp, which are generated by the radiation image capturing apparatus 1 with no grid Gr attached (or the image processing apparatus C) irradiated with radiation emitted from the irradiation apparatus 52, and then performs a low-pass filter process on the pixel values Vp of the pixels of the radiation image P using a scattering kernel (also called the "convolution kernel", "convolution matrix", "two-dimensional convolution kernel", etc.), thereby generating a low frequency image P1f as shown in FIG. 6.

Also, the image processing apparatus C estimates the body thickness Th of the subject H based on the generated radiation image P or based on the signal values Sp for the respective pixels of the radiation image P, namely, the signal values Sp based on which the pixel values Vp of the respective pixels of the radiation image P are calculated as described above. Then, the image processing apparatus C estimates scattered ray content rates r for the respective pixels of the radiation image P based on the estimated body thickness Th of the subject H. Then, the image processing apparatus C calculates scattered ray components Cs for the respective pixels of the radiation image P based on the generated low frequency image P1f and the estimated scattered ray content rates r, and subtracts the calculated scattered ray components Cs from the respective pixel values Vp of the radiation image P, thereby generating a radiation image P* (a second radiation image) with the scattered ray components Cs (i.e., scattered rays) removed (hereinafter simply referred to as the "radiation image P*").

In the embodiments, as described above, the image processing apparatus C estimates the body thickness Th of the subject H based on the radiation image P or the signal values Sp for the respective pixels of the radiation image P. Hereinafter, a method for estimating the body thickness Th of the subject H (i.e. a body thickness estimation method) is detailed using some instances. Effects of the radiation image capturing system 50 according to the embodiments are also described.

First Embodiment

Figure 7A:
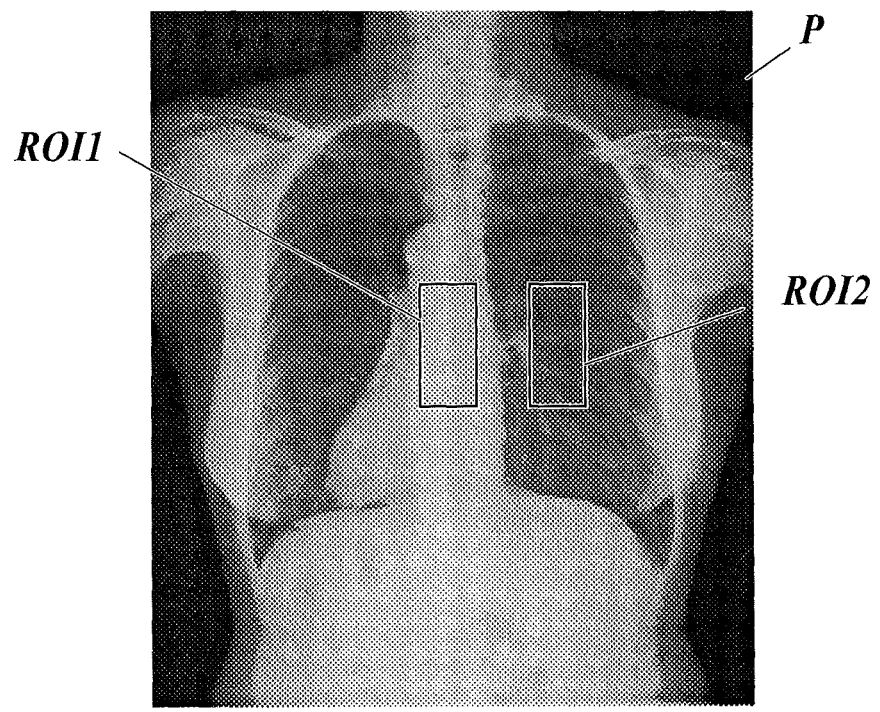
FIG. 7A shows an example of two regions of interest set at two parts in a radiation image.

In the first embodiment, as shown in FIG. 7A, the image processing apparatus C (i) sets regions of interest ROI1, ROI2 at two parts in the radiation image P generated as described above, the two parts having different pixel values Vp as a whole, (ii) throws signal values Sp for respective pixels belonging to the regions of interest ROI1, ROI2 (i.e., the signal value Sp based on which the pixel value Vp of each pixel of the radiation image P is calculated) into a histogram, (iii) calculates a characteristic amount from the histogram and (iv) estimates the body thickness Th of the subject H based on the characteristic amount. Hereinafter, details are described.

As the regions of interest ROI1, ROI2, in the radiation image P, the region of interest ROI1 is set at a part having a small pixel value Vp (or signal value Sp) as a whole, and the region of interest ROI2 is set at a part having a larger pixel value Vp (or signal value Sp) as a whole than the region of interest ROI1, for example. That is, as shown in FIG. 7A as an example, one region of interest, ROI1, is set at a region where the spinal column and centrums are captured and accordingly which contains mainly small pixel values Vp (signal values Sp), and another region of interest, ROI2, is set at a region where the lung field is captured and accordingly which mainly contains larger pixel values Vp (signal values Sp) than the region of interest ROI1.

Figure 7B:
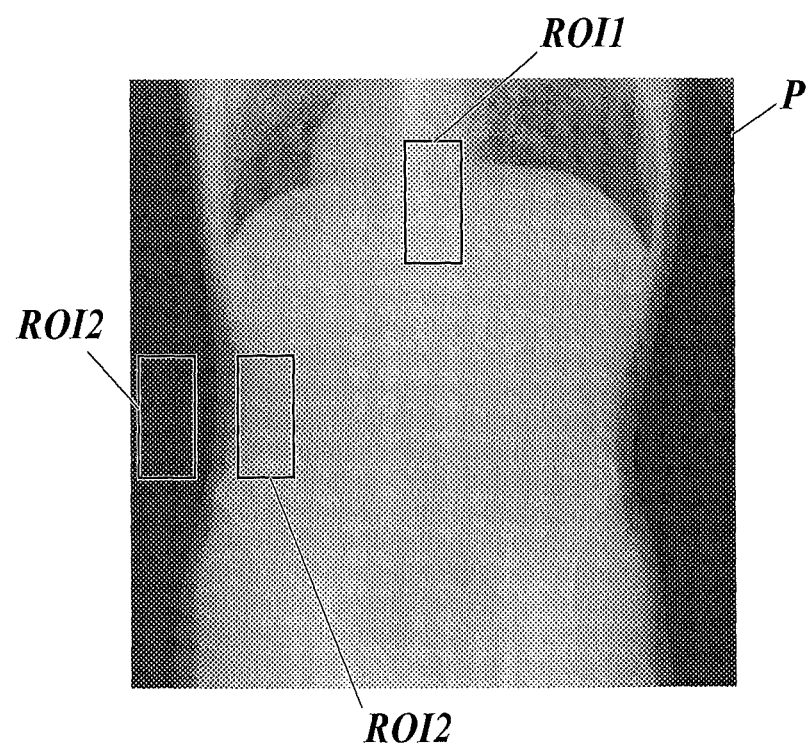
FIG. 7B shows an example(s) of two regions of interest set at two parts in a radiation image.

The above one region of interest, ROI1, may be set at a part where a bone(s) other than the spinal column or centrums (the skull in the head, the humerus in an arm, the femur in a leg, etc.) is captured. Further, if the lung field or the like is not captured in the radiation image P, as shown in FIG. 7B as an example, the above other region of interest, ROI2, may be set at a part where the flank (in the case where the captured region is the front of the abdomen, etc.) is captured or at a through part (in the case where the captured region is the head, abdomen, arm, leg, etc.) in the radiation image P, namely, a part in the radiation image P corresponding to a directly irradiated part in the radiation image capturing apparatus 1, not via the subject H.

In the embodiment, the parts where the regions of interest ROI1, ROI2 are set in the radiation image P are predetermined for each captured region (head, chest, abdomen, arm, leg, hand, foot, etc.). When the console C, namely, the image processing apparatus C, obtains information on the captured region from photography order information (also called "photography condition key", etc.), which is information on radiation image capturing, or the like, the console C sets, in the radiation image P, the regions of interest ROI1, ROI2 at the parts predetermined for the captured region.

Then, the image processing apparatus C throws the signal values Sp for the respective pixels belonging to the regions of interest ROI1, ROI2 into a histogram. The class width of the histogram is appropriately determined. Distribution of frequencies F when the signal values Sp for the respective pixels belonging to the regions of interest ROI1, ROI2 are thrown into a histogram is, for example, distribution shown in FIG. 8A if the body thickness Th of the subject H is large or distribution shown in FIG. 8B if the body thickness Th of the subject H is small.

Figure 9A:
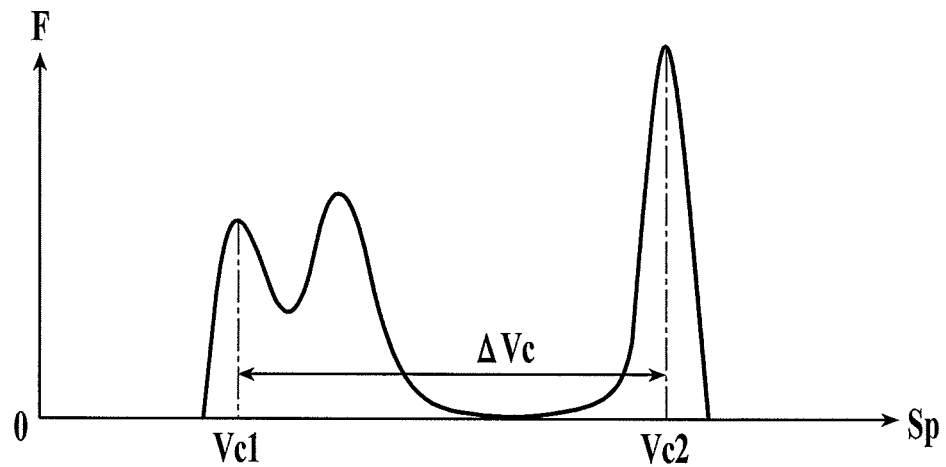
FIG. 9A shows an example of distribution of frequencies on a histogram if the body thickness of a subject is large.
Figure 9B:
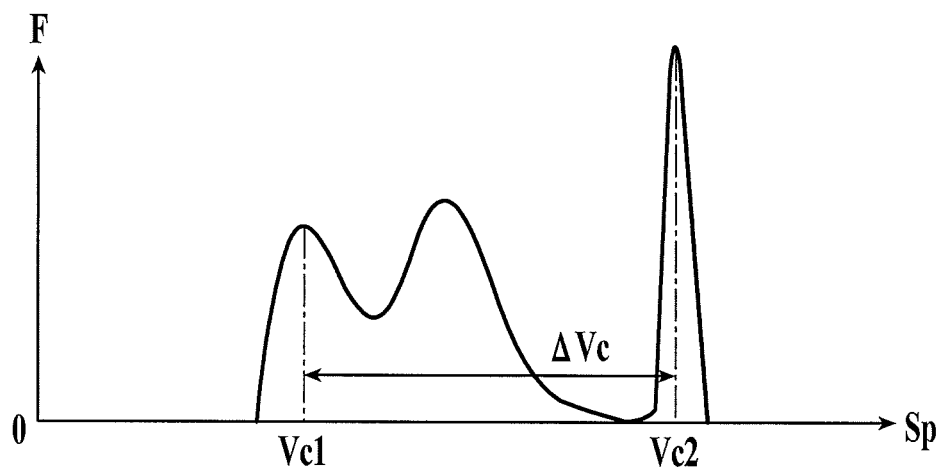
FIG. 9B shows an example of distribution of frequencies on a histogram if the body thickness of a subject is small.

Because, as described above, the regions of interest ROI1, ROI2 are set at a part having a small pixel value Vp (or signal value Sp) as a whole and a part having a large pixel value Vp (or signal value Sp) as a whole in the radiation image P, respectively, at least two peaks appear in the distribution of frequencies F. As shown in FIG. 9A and FIG. 9B, described below, three peaks may appear in the distribution of frequencies F, or although not shown, only one peak may appear in the distribution of frequencies F.

Figure 8A:
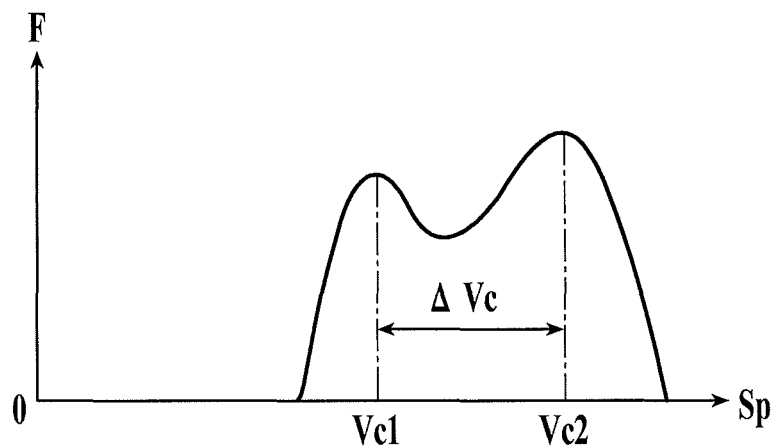
FIG. 8A shows an example of distribution of frequencies on a histogram if the body thickness of a subject is large.

The image processing apparatus C is configured to calculate the difference between two signal values serving as references in the distribution of frequencies F on the histogram as a characteristic amount calculated from the histogram, and estimate the body thickness Th of the subject H based on the difference. The difference between two signal values serving as references in the distribution of frequencies F is, for example, the difference ΔVc between class values Vc1, Vc2 respectively corresponding to the representative values of the regions of interest ROI1, ROI2 appearing in the distribution of frequencies F as shown in FIG. 8A and FIG. 8B.

Figure 8B:
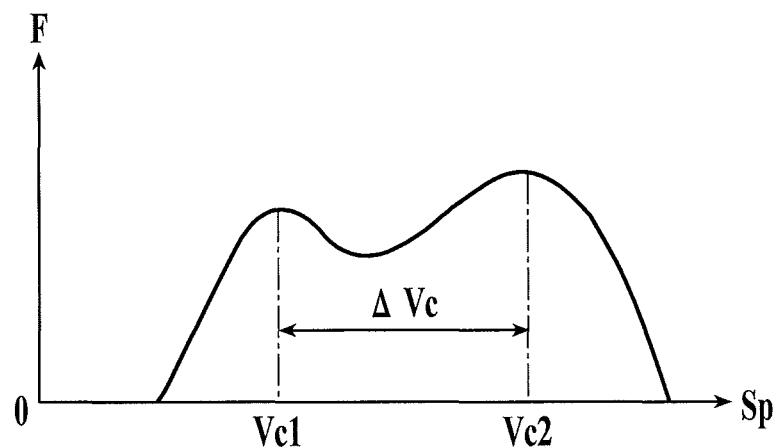
FIG. 8B shows an example of distribution of frequencies on a histogram if the body thickness of a subject is small.

Thus, it is known that, as shown in FIG. 7A, when the region of interest ROI1 is set, for example, at a part where the spinal column and centrums are captured, and the region of interest ROI2 is set, for example, at a part where the lung field is captured; or, as shown in FIG. 7B, when the region of interest ROI1 is set, for example, at a part where the spinal column and centrums are captured, and the region of interest ROI2 is set, for example, at a part where the flank is captured, the magnitude of the difference ΔVc between the class values Vc1, Vc2 respectively corresponding to the representative values of the regions of interest ROI1, ROI2 differs between the case where the body thickness Th of the subject H is large (shown in FIG. 8A) and the case where the body thickness Th of the subject H is small (shown in FIG. 8B). The larger the body thickness Th is, the smaller the difference ΔVc is.

Meanwhile, according to the studies of the inventors of this application, it has been found that, as shown in FIG. 7B, when the region of interest ROI1 is set at a part where the spinal column and centrums are captured and the region of interest ROI2 is set at a through part (the signal values Sp for which are not saturated) too, the magnitude of the difference ΔVc between the class values Vc1, Vc2 respectively corresponding to the representative values of the regions of interest ROI1, ROI2 differs between the case where the body thickness Th of the subject H is large (shown in FIG. 9A) and the case where the body thickness Th of the subject H is small (shown in FIG. 9B). However, the larger the body thickness Th is, the larger the difference ΔVc is.

The reason why the difference ΔVc is larger as the body thickness Th is larger when the region of interest ROI2 is set at a through part (shown in FIG. 9A and FIG. 9B) whereas the difference ΔVc is smaller as the body thickness Th is larger when the region of interest ROI2 is set at a part corresponding to the inside of the body of the subject H (i.e., the lung field, flank, etc.) is unclear, but can be considered as follows: this phenomenon occurs because, as the body thickness Th of the subject H is larger, more scattered rays are present and accordingly the signal value(s) Sp is larger, whereas, originally, the signal value(s) Sp is small when the body thickness Th of the subject H is large as compared with when the body thickness Th of the subject H is small.

Figure 10A:
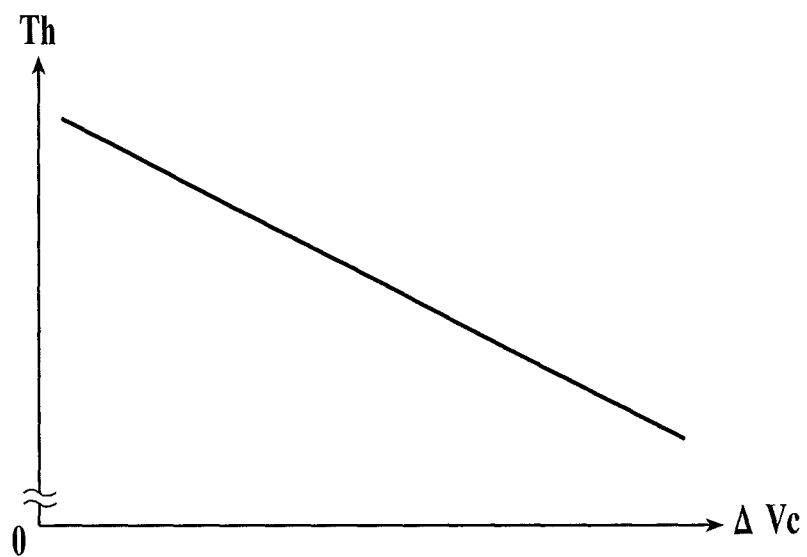
FIG. 10A is a graph showing an example of a relationship between subject body thickness Th and difference ΔVc.
Figure 10B:
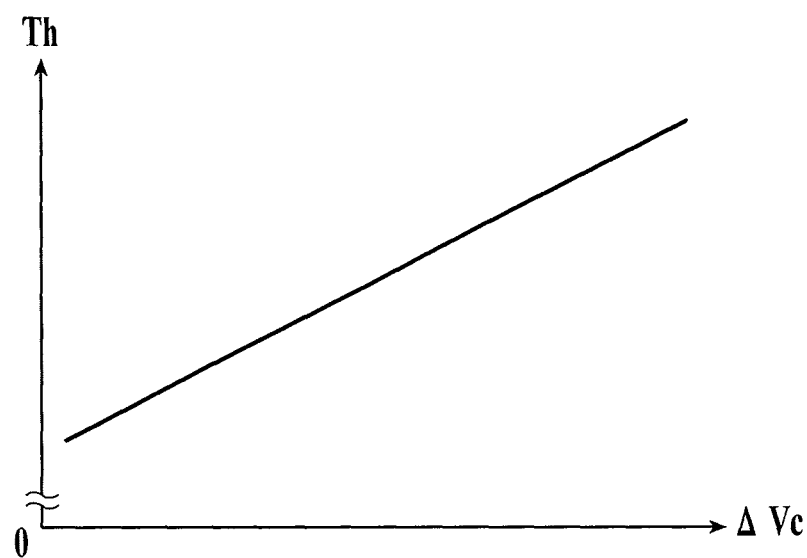
FIG. 10B is a graph showing an example of a relationship between subject body thickness Th and difference ΔVc.

In the first embodiment, the image processing apparatus C obtains the relationship between the body thickness Th and the difference ΔVc in advance by experiments, thereby obtaining the relationship(s) as shown in FIG. 10A and FIG. 10B, and stores the relationship(s) in a storage unit such as a ROM. The image processing apparatus C may store the relationship(s) in the form of a graph(s) as shown in FIG. 10A and FIG. 10B, table(s) or the like, or may store the relationship(s) in the form of a function(s).

The relationship between the body thickness Th and the difference ΔVc shown in FIG. 10A is for the case where the regions of interest ROI1, ROI2 are set such that the larger the body thickness Th is, the smaller the difference ΔVc is, and the relationship between the body thickness Th and the difference ΔVc shown in FIG. 10B is for the case where the regions of interest ROI1, ROI2 are set such that the larger the body thickness Th is, the larger the difference ΔVc is. The relationship between the body thickness Th and the difference ΔVc is not always a linear relationship as shown in FIG. 10A and FIG. 10B. Further, the above relationship(s) may change according to the irradiation apparatus 52 (shown in FIG. 3) or the tubular lamp used for radiation image capturing. In such a case, the image processing apparatus C may have the above relationship(s) for each irradiation apparatus 52 or tubular lamp.

The image processing apparatus C is configured to, when calculates the difference ΔVc between the class values Vc1, Vc2 as described above, refer to the relationship between the body thickness Th and the difference ΔVc so as to obtain the body thickness Th of the subject H at the calculated difference ΔVc, thereby estimating the body thickness Th of the subject H, for example.

[Effects]

As described above, the radiation image capturing system 50 or the body thickness (Th) estimation method according to the first embodiment (i) sets the regions of interest ROI1, ROI2 at two parts in the radiation image P, respectively, (ii) throws the signal values Sp for the respective pixels belonging to the regions of interest ROI1, ROI2 into a histogram, (iii) calculates the characteristic amount (the difference ΔVc between the class values Vc1, Vc2 respectively corresponding to the representative values of the regions of interest ROI1, ROI2 appearing in the distribution of frequencies F) from the histogram and (iv) estimates the body thickness Th of the subject H based on the characteristic amount. This makes it possible to accurately estimate the body thickness Th of the subject H by image analysis of the captured radiation image P, without use of a sensor or the like.

Further, it is possible to: accurately estimate the scattered ray content rates r for the respective pixels of the radiation image P based on the accurately estimated body thickness Th of the subject H; accurately calculate the scattered ray components Cs for the respective pixels of the radiation image P based on the generated low frequency image P1f (shown in FIG. 6) and the estimated scattered ray content rates r; and accurately generate the radiation image P* by subtracting the calculated scattered ray components Cs from the respective pixel values Vp of the radiation image P.

In the first embodiment, the regions of interest ROI1, ROI2 are set at two parts in the generated radiation image P. However, the regions of interest may be set at three or more parts in the radiation image P. To this case too, the above is applicable. Alternatively, the region(s) of interest (ROI) may be set at one part only in the radiation image P. In this case too, when the signal values Sp for the respective pixels belonging to the region of interest ROI are thrown into a histogram, as shown in FIG. 8A, FIG. 8B, FIG. 9A and FIG. 9B, a plurality of peaks may appear in the distribution of frequencies F, and accordingly a plurality of representative values of the region of interest ROI may be obtained. Hence, the radiation image capturing system 50 or the body thickness estimation method according to the embodiment may be configured to extract two representative values from these representative values, calculate the difference between the extracted two representative values as the characteristic amount, and estimate the body thickness Th of the subject H based on the characteristic amount.

Further, in the first embodiment, as the characteristic amount calculated from the histogram, attention is paid to the magnitude of the difference ΔVc between the class values Vc1, Vc2 respectively corresponding to the representative values of the regions of interest ROI1, ROI2. It is possible, however, to calculate, as the characteristic amount calculated from the histogram, the ratio of the class values Vc1, Vc2 respectively corresponding to the representative values of the regions of interest ROI1, ROI2 and/or the standard deviation, the difference between the mean values of the signal values for the respective pixels belonging to the respective regions of interest ROI1, ROI2 and/or the ratio, and/or the like, and estimate the body thickness Th of the subject H based on any of these.

[Modification]

By the way, the inventors of this application have studied and found out that the body thickness Th of the subject H estimated as described in the first embodiment sometimes has an error ΔTh. Then, the inventors of this application have further studied about this error ΔTh and found out that there is a tendency that the larger the density correction value S (in the formula (2)) is, the larger the error ΔTh is. The density correction value S is used in conversion of the signal values Sp generated for the respective pixels (radiation detection elements 7) of the radiation image capturing apparatus 1 into the normalized data Sp* by normalization.

Figure 11:
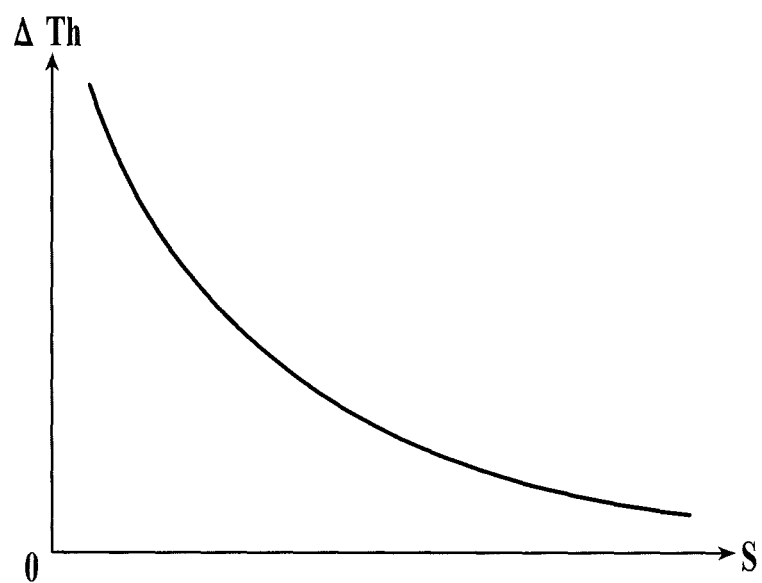
FIG. 11 is a graph showing an example of a relationship between density correction value S and correction value ΔTh.

Hence, in addition to the relationship between the body thickness Th and the difference ΔVc (shown in FIG. 10A and FIG. 10B), the image processing apparatus C obtains the relationship between the density correction value S and the error ΔTh (i.e., the correction value ΔTh) in advance by experiments, thereby obtaining the relationship as shown in FIG. 11, and stores the relationship in the storage unit such as a ROM. The image processing apparatus C may store this relationship in the form of a graph as shown in FIG. 11, table or the like, or may store the relationship in the form of a function. Further, the image processing apparatus C may have the above relationship for each irradiation apparatus 52 or tubular lamp.

The image processing apparatus C refers to the relationship between the density correction value S and the correction value ΔTh so as to obtain the correction value ΔTh at the density correction value S used in normalization of the signal values Sp, and adds the correction value ΔTh to the body thickness Th of the subject H estimated based on the difference ΔVc between the class values Vc1, Vc2 as described above, thereby correcting the estimated body thickness Th of the subject H with the correction value ΔTh, namely, re-estimating the body thickness Th (Th+ΔTh, in this case) of the subject H. This makes it possible to more accurately estimate the body thickness Th of the subject H.

Second Embodiment

The image processing apparatus C can be configured to, when, as shown in FIG. 7B, the abdomen of the subject H is captured in the radiation image P, estimate the body thickness Th of the subject H based on information on the shape (hereinafter "shape information") of the subject H captured in the radiation image P. The shape information on the subject H is, for example, the width W of the abdomen of the subject H.

Figure 12A:
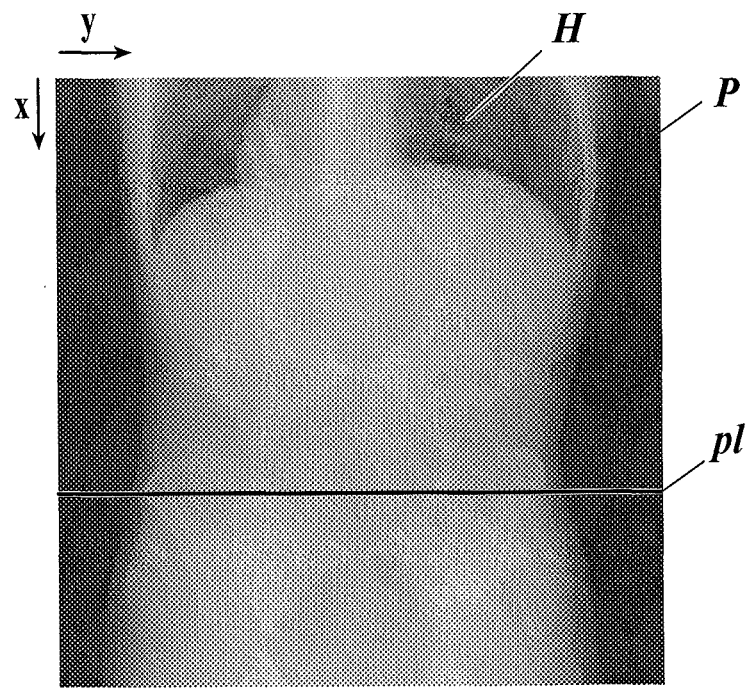
FIG. 12A is an illustration for explaining a pixel row at the position of the abdomen of a subject captured in a radiation image.

In this case, the image processing apparatus C (i) identifies the position of the abdomen of the subject H captured in the radiation image P based on the positions or the like of the spinal column, centrums, lung field, pelvis and so forth of the subject H captured in the radiation image P, (ii) extracts pixel values Vp (x, y) of respective pixels (x, y) of a pixel row p1 at the position of the abdomen of the subject H as shown in FIG. 12A and (iii) plots the pixel values Vp against y.

Then, the image processing apparatus C, of the profile of the pixel values Vp (x, y), approximates the pixel values Vp (x, y) of a part A where the subject H is captured with a quadratic function or the like and approximates the pixel values Vp (x, y) of each through part B with a straight line, obtains the distance Δy between two intersection points of the quadratic function with the respective straight lines, and converts the distance Δy into the width W of the abdomen of the subject H, thereby calculating the width W thereof. Instead of the quadratic function, the profile of the pixel values Vp (x, y) may be approximated with another curve such as a quartic function or an ellipse.

Figure 13:
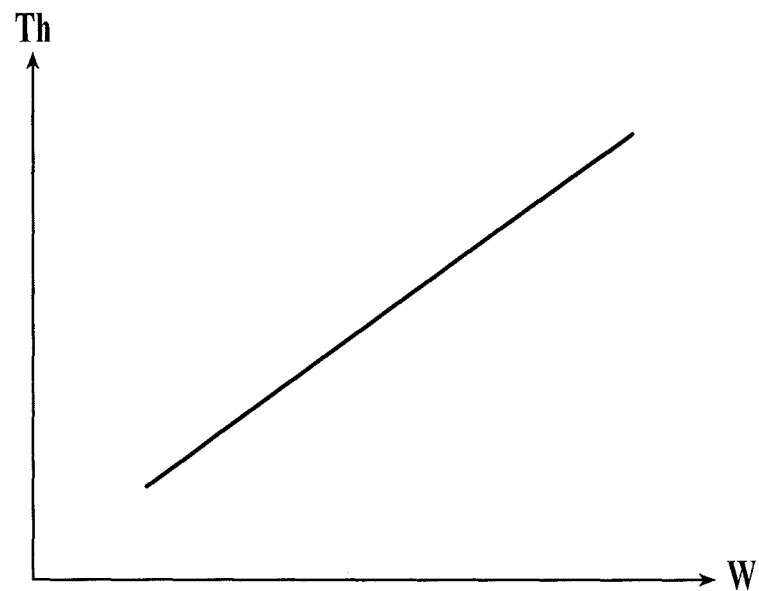
FIG. 13 is a graph showing an example of a relationship between subject abdomen width W and subject body thickness Th.

The image processing apparatus C obtains the relationship between the abdomen width W and the body thickness Th in advance by experiments, thereby obtaining the relationship as shown in FIG. 13, and stores the relationship in the storage unit such as an ROM. The image processing apparatus C is configured to, when calculates the width W of the abdomen of the subject H as described above, refer to the relationship, thereby estimating the body thickness Th of the subject H based on the width W of the abdomen of the subject H, for example.

In the above configuration example, the body thickness Th of the subject H is estimated based on the width W of the abdomen of the subject H as the shape information on the subject H. It is possible, however, to calculate, as the shape information on the subject H, the curvature or the radius of the curvature of a curve with which, of the profile of the pixel values Vp (x, y), the part A where the subject H is captured is approximated. The shape information can be any as long as the body thickness Th of the subject H can be estimated based thereon.

[Effects]

As described above, the radiation image capturing system 50 or the body thickness (Th) estimation method according to the second embodiment can accurately estimate the body thickness Th of the subject H based on the shape information on the subject H (e.g., the width W of the abdomen of the subject H) captured in the radiation image P.

Further, it is possible to: accurately estimate the scattered ray content rates r for the respective pixels of the radiation image P based on the accurately estimated body thickness Th of the subject H; accurately calculate the scattered ray components Cs for the respective pixels of the radiation image P based on the generated low frequency image P1$f$ (shown in FIG. 6) and the estimated scattered ray content rates r; and accurately generate the radiation image P* by subtracting the calculated scattered ray components Cs from the respective pixel values Vp of the radiation image P.

[Modification]

Figure 12B:
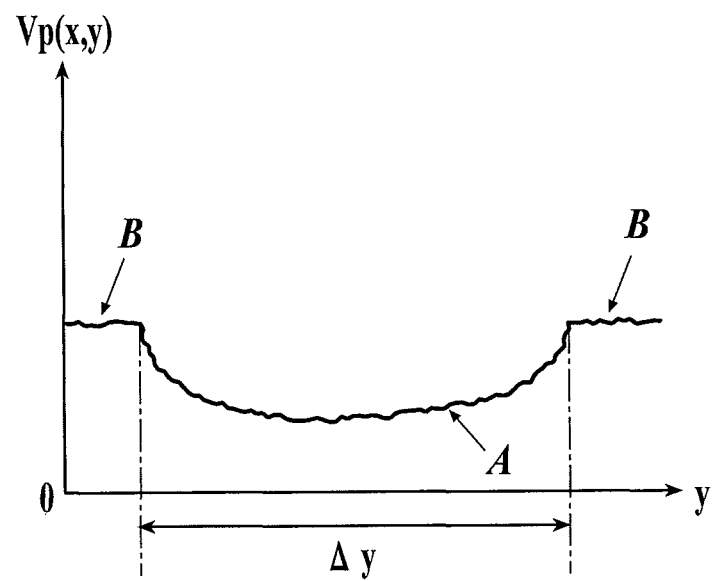
FIG. 12B is a graph showing a profile of pixel values of the pixel row.

In the second embodiment, as shown in FIG. 12A and FIG. 12B, the width W of the abdomen of the subject H is calculated from the distance Δy between two intersection points of the curve used for approximation of the pixel values Vp (x, y) of the part A where the subject H is captured with the respective straight lines used for approximation of the pixel values Vp (x, y) of the through parts B, of the profile of the pixel values Vp (x, y), as the shape information on the subject H. However, there is a case where the width W of the subject H is too large to capture the edge(s) of the subject H in the width direction in the radiation image P. That is, there is a case where no through part is captured in the radiation image P.

In such a case, for example, the image processing apparatus C (i) identifies the position of the abdomen of the subject H captured in the radiation image P based on the positions or the like of the spinal column, centrums, lung field, pelvis and so forth of the subject H captured in the radiation image P, (ii) extracts the pixel values Vp (x, y) of the respective pixels (x, y) of the pixel row p1 at the position of the abdomen of the subject H and (iii) plots the pixel values Vp against y, as described above. Then, the image processing apparatus C approximates the pixel values Vp with a curve such as a quadratic function, as described above.

Because no through part is captured in the radiation image P, the above-described approximation of the profile of the pixel values Vp (x, y) with straight lines cannot be performed. Then, for example, the image processing apparatus C calculates the dose of the radiation per unit area emitted from the irradiation apparatus 52 to the radiation image capturing apparatus 1 based on, for example, (i) a tube voltage and (ii) an mAs value (i.e., tube current x radiation emission time) set in the irradiation apparatus 52 (shown in FIG. 3) in capturing the radiation image P and (iii) the distance SID between the irradiation apparatus 52 and the radiation image capturing apparatus 1 in capturing the radiation image P, and thereby can estimate pixel values supposing that the radiation image capturing apparatus 1 is irradiated with radiation emitted from the irradiation apparatus 52 not via the subject H (i.e., pixel values of through parts if they are captured in the radiation image P in that situation).

The image processing apparatus C can thus estimate the pixel values of the hypothetical through parts, which are hypothetically captured in the radiation image P, obtain the distance Δy between two intersection points of the above approximate curve with the respective straight lines representing the estimated pixel values, and calculate the width W of the abdomen of the subject H therefrom.

According to the configuration of this modification, even if the width W of the subject H is too large to capture the edge(s) of the subject H in the width direction in the radiation image P, it is possible to: accurately estimate the width W of the abdomen of the subject H based on the hypothetical through parts, which are hypothetically captured in the radiation image P, and the profile of the pixel values Vp (x, y) of the respective pixels of the pixel row at the position of the abdomen of the subject H identified in the radiation image P; and accurately estimate the body thickness Th of the subject H based thereon.

Third Embodiment

The image processing apparatus C can adopt one of the estimation processes of the body thickness Th of the subject H of the first embodiment and the second embodiment so as to estimate the body thickness Th of the subject H. However, the image processing apparatus C can be configured to use the estimation processes of the body thickness Th of the subject H of the first embodiment and the second embodiment complementarily.

That is, for example, the image processing apparatus C is configured to basically perform the estimation process of the body thickness Th of the subject H of the first embodiment. That is, the image processing apparatus C (i) sets the regions of interest ROI1, ROI2 at two parts in the radiation image P, (ii) throws the signal values Sp for the respective pixels belonging to the regions of interest ROI1, ROI2 into a histogram, (iii) calculates the characteristic amount (e.g., the difference ΔVc) (or that corrected with the correction value ΔTh) from the histogram and (iv) estimates the body thickness Th of the subject H based on the characteristic amount.

However, for example, in the case shown in FIG. 7A, there is a case where the body thickness Th of the subject H cannot be estimated based on the characteristic amount, or even if it can, the estimated body thickness Th of the subject H is an abnormal value. For example, if water builds up in the lung field of a patient, who is the subject H, there is little difference between the signal values Sp for the respective pixels belonging to the region of interest ROI2 set at a part where the lung field is captured and the signal values Sp for the respective pixels belonging to the region of interest ROI1 set a part where the centrums and so forth are captured. Because the difference therebetween is so small, when the signal values Sp are thrown into a histogram, two peaks do not appear, and instead: one peak appears; on the contrary, many peaks appear; or distribution of frequencies F forms a trapezoid, so that the characteristic amount to be calculated from the histogram cannot be calculated.

Further, for example, in the case shown in FIG. 7B too, there is a case where the body thickness Th of the subject H cannot be estimated; for example, there is little difference between the signal values Sp for the respective pixels belonging to the region of interest ROI2 set at a part where the flank is captured and the signal values Sp for the respective pixels belonging to the region of interest ROI1 set a part where the centrums and so forth are captured. Further, there is a case where the region of interest ROI2 cannot be set; for example, the width W of the subject H is too large to capture a through part(s) in the radiation image P.

Hence, the image processing apparatus C is configured to, when determines that the body thickness Th of the subject H cannot be accurately estimated with the estimation process of the body thickness Th of the subject H of the first embodiment, estimate the body thickness Th of the subject H with the estimation process of the body thickness Th of the subject H of the second embodiment.

Alternatively, the image processing apparatus C may be configured to basically perform the estimation process of the body thickness Th of the subject H of the second embodiment. That is, the image processing apparatus C basically estimates the body thickness Th of the subject H based on the shape information on the subject H, such as the width W of the abdomen of the subject H obtained as described above.

However, there is a case where the body thickness Th of the subject H cannot be estimated based on the shape information on the subject H, or even if it can, the estimated body thickness Th of the subject H is an abnormal value; for example, a region as the object from which the shape information on the subject H is obtained, such as the abdomen of the subject H, is not captured in the radiation image P, or, as described above, the width W of the subject H is too large to fit inside the radiation image P.

Hence, the image processing apparatus C is configured to, when determines that the body thickness Th of the subject H cannot be accurately estimated with the estimation process of the body thickness Th of the subject H of the second embodiment, estimate the body thickness Th of the subject H with the estimation process of the body thickness Th of the subject H of the first embodiment.

[Effects]

As described above, in the radiation image capturing system 50 or the body thickness (Th) estimation method according to the third embodiment, the image processing apparatus C is configured to use the estimation processes of the body thickness Th of the subject H of the first embodiment and the second embodiment complementarily. This makes it possible to, when one of the estimation processes of the body thickness Th of the subject H cannot be used or can be used but cannot accurately estimate the body thickness Th of the subject H, use the other thereof, and accordingly can accurately estimate the body thickness Th of the subject H.

Further, it is possible to: accurately estimate the scattered ray content rates r for the respective pixels of the radiation image P based on the accurately estimated body thickness Th of the subject H; accurately calculate the scattered ray components Cs for the respective pixels of the radiation image P based on the generated low frequency image P1$f$ (shown in FIG. 6) and the estimated scattered ray content rates r; and accurately generate the radiation image P* by subtracting the calculated scattered ray components Cs from the respective pixel values Vp of the radiation image P.

The image processing apparatus C may be configured to automatically and appropriately change the parameters used in the algorism (shown in FIG. 6) for the removal of scattered rays, based on, for example, the information obtained by image analysis of the radiation image P, the photography condition obtained from the photography order information, and/or the photography condition obtained from the irradiation apparatus 52 side.

Further, the image processing apparatus C may be configured to change the scattering kernel used for the low-pass filter process performed on the generated radiation image P, thereby generating the low frequency image P1$f$, according to the body thickness Th of the subject H estimated as described above.

[Process on Radiation Image P*]

As described above, the image processing apparatus C estimates the body thickness Th of the subject H, estimates the scattered ray content rates r for the respective pixels of the radiation image P based on the accurately estimated body thickness Th of the subject H, calculates the scattered ray components Cs for the respective pixels of the radiation image P based on the generated low frequency image P1$f$ and the estimated scattered ray content rates r as shown in FIG. 6. Then, the image processing apparatus C subtracts the calculated scattered ray components Cs from the respective pixel values Vp of the radiation image P, and thereby can accurately generate the radiation image P* with the scattered ray components Cs removed.

Figure 14:
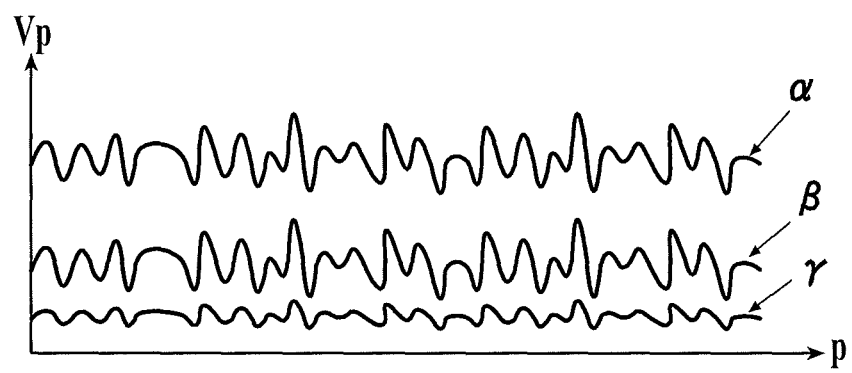
FIG. 14 shows pixel values of pixels of an original radiation image captured by the radiation image capturing apparatus with no grid attached (α), pixel values of the pixels of the radiation image with scattered ray components removed (β) and pixel values of pixels of a radiation image captured by the radiation image capturing apparatus with a grid attached (γ)

However, even on the radiation image P*, X-ray quantum noise is still superimposed. As described above, the scattered ray components Cs are subtracted from the radiation image P, and thereby, as shown in FIG. 14, the pixel values Vp of the pixels p of the original radiation image P ($\alpha$ in FIG. 14) become smaller overall ($\beta$ in FIG. 14) and therefore the pixel values Vp of the pixels p of the radiation image P* ($\beta$ in FIG. 14) are about the same as pixel values Vp of pixels p of a radiation image P captured by the radiation image capturing apparatus 1 with the grid Gr attached ($\gamma$ in FIG. 14). Although the pixel values Vp are smaller overall in the radiation image P* than in the original radiation image P, the amount of the X-ray quantum noise on the radiation image P* is the same as that of the X-ray quantum noise on the original radiation image P. Therefore, the apparent signal-to-noise ratio is worse in the radiation image P*, and therefore graininess of the radiation image P* may be low.

In such a case, the image processing apparatus C is configured to perform a noise reduction process (i.e., noise reduction) on the pixel values Vp of the generated radiation image P*. As the noise reduction, for example, statistical filtering such as Wiener filtering may be performed on the pixel values Vp of the radiation image P*.

When Wiener filtering is performed, as it is well known, variance $\sigma v$ of noise (X-ray quantum noise, in this case) needs to be set. In the above embodiments and modifications, for example, a value suitable for the scattered ray components Cs estimated for the respective pixels as described above can be set as the variance $\sigma v$ of noise.

With this configuration, the scattered ray components Cs are subtracted from the original radiation image P by the removal of scattered rays, and thereby, as shown in FIG. 14, the pixel values Vp of the original radiation image P ($\alpha$ in FIG. 14) become smaller overall (β in FIG. 14) and therefore the pixel values Vp of the radiation image P* (β in FIG. 14) are about the same as pixel values Vp of the radiation image P captured by the radiation image capturing apparatus 1 with the grid Gr attached (γ in FIG. 14), and also the noise superimposed on the radiation image P* is reduced overall by the noise reduction.

Thus, the noise superimposed on the radiation image P* can be reduced to the same level as that superimposed on the radiation image P captured by the radiation image capturing apparatus 1 with the grid Gr attached. Hence, the apparent signal-to-noise ratio can be properly prevented from being worse in the radiation image P*, and therefore graininess of the radiation image P* can be the same level as that of the radiation image P captured by the radiation image capturing apparatus 1 with the grid Gr attached.

As described in the above-mentioned Japanese Patent Application Publication No. 2014-207958 and so forth, when radiation image capturing is performed by the radiation image capturing apparatus 1 with the grid Gr attached, scattered rays caused by the subject H are removed (i.e., scattered rays do not reach the radiation image capturing apparatus 1 with the grid Gr attached), and also direct rays (also called "primary rays", etc.), which are emitted from the irradiation apparatus 52, and, without being scattered by the subject H, pass through the subject H and reach the radiation image capturing apparatus 1 with the grid Gr attached, are cut to some extent.

As shown in FIG. 14, by subtracting the scattered ray component Cs from the generated radiation image P, the pixel values Vp of the original radiation image P (α in FIG. 14) become smaller overall (β in FIG. 14) and therefore the pixel values Vp of the radiation image P* (β in FIG. 14) are close to pixel values Vp of the radiation image P captured by the radiation image capturing apparatus 1 with the grid Gr attached (γ in FIG. 14) but, as shown in FIG. 14, could be somewhat larger than the pixel values Vp of the radiation image P captured by the radiation image capturing apparatus 1 with the grid Gr attached.

Hence, from the radiation image P* with the scattered ray components Cs removed by the removal of scattered rays (shown in FIG. 6) or a not-shown radiation image P** with the scattered ray components Cs and the X-ray quantum noise removed, the direct ray components may further be removed.

The direct ray components can be removed, for example, by multiplying the pixel values Vp of the pixels p of the radiation image P* or P** by a preset fixed rate (0<δ<1).

The rate δ, by which the pixel values Vp of the pixels p of the radiation image P* or P** are multiplied, may vary according to the pixel values Vp. That is, for example, the rate δ may be preset such that the larger the pixel value Vp of each pixel p of the radiation image P* or P** is, the larger the rate δ is; to put it the other way around, the smaller the pixel value Vp of each pixel p of the radiation image P* or P** is, the smaller the rate δ is, and hence the pixel value Vp of each pixel p of the radiation image P* or P** can be multiplied by the rate δ for the pixel value Vp.

With this configuration, the pixel values Vp of (i) the radiation image P*, generated by subjecting the radiation image P captured by the radiation image capturing apparatus 1 with no grid Gr attached to the removal of scattered rays, or (ii) the radiation image P**, generated by subjecting the radiation image P* to the X-ray quantum noise reduction, can be around the pixel values Vp of the radiation image P captured by the radiation image capturing apparatus 1 with the grid Gr attached.

Consequently, for example, the radiation image P obtained by photographing a patient with the radiation image capturing apparatus 1 with the grid Gr attached in a radiography room or the like and the radiation image P* or P** obtained by photographing the same patient with the radiation image capturing apparatus 1 with no grid Gr attached in the hospital ward Ra or the like and performing the removal of scattered rays and so forth are substantially the same. Therefore, when a doctor or the like compares these images with one another, he/she can make an accurate diagnosis without feeling strange.

Needless to say, the present invention is not limited to the above embodiments and so forth and hence can be appropriately modified within a scope not departing from the spirit of the present invention.

What is claimed is:

1. An x-ray image capturing system comprising:
an x-ray image capturing apparatus including:
a plurality of x-ray detection elements which are arranged two-dimensionally and generate electric charge according to a dose of x-rays with which the x-ray detection elements are irradiated; and
a control unit which converts the electric charge generated in each of the x-ray detection elements into a signal value;
an irradiation apparatus which, passing x-rays through a subject, irradiates the x-ray image capturing apparatus with the x-rays; and
an image processing apparatus which generates a first x-ray image based on the signal values, which corresponds to the electric charge generated in each of the x-ray detection elements, wherein
the image processing apparatus:
generates the first x-ray image based on the signal values generated by irradiating the x-ray image capturing apparatus with the irradiation apparatus, wherein there is no grid attached to the image capturing apparatus;
performs a low-pass filter process on a pixel values of the first x-ray image using a scattering kernel, thereby generating a low frequency image;
estimates a body thickness of the subject based on the signal values;
estimates a scattered ray content rate based on the body thickness;
calculates a scattered ray component in the first x-ray image based on the low frequency image and the scattered ray content rate; and
subtracts the scattered ray component from the first x-ray image, thereby generating a second x-ray image with the scattered ray component removed; and
wherein the image processing apparatus (i) sets two regions of interest at different parts in the first x-ray image, a second region of interest of the two regions of interest having mainly larger pixel values relative to a first region of interest of the two regions of interest (ii) creates a histogram from both the signal values of each pixel belonging to the first region of interest and the signal values of each pixel belonging to the second region of interest, (iii) calculates a characteristic amount from the histogram and (iv) estimates the body thickness based on the characteristic amount, the characteristic amount being a difference between two signal values serving as references in a distribution of frequencies on the histogram.

2. The x-ray image capturing system according to claim 1, wherein when the image processing apparatus cannot estimate the body thickness based on the characteristic amount, the image processing apparatus estimates the body thickness based on shape information of the subject captured in the first x-ray image.

3. The x-ray image capturing system according to claim 1, wherein when the image processing apparatus cannot estimate the body thickness based on the shape information, the image processing apparatus (i) sets a region of interest at one part or multiple parts in the first x-ray image, (ii) creates a histogram from the signal values of each pixel belonging to the region of interest, (iii) calculates a characteristic amount from the histogram and (iv) estimates the body thickness based on the characteristic amount, the characteristic amount being a difference between two signal values serving as references in a distribution of frequencies on the histogram.

4. The x-ray image capturing system according to claim 1, wherein the characteristic amount is a difference between two signal values serving as references in distribution of frequency on the histogram.

5. The x-ray image capturing system according to claim 4, wherein the image processing apparatus corrects the body thickness, which is estimated based on the difference, based on a density correction value used in normalization of the signal values, thereby re-estimating the body thickness.

6. The x-ray image capturing system according to claim 2, wherein the shape information is a width of an abdomen of the subject.

7. The x-ray image capturing system according to claim 6, wherein when no edge of the subject in a width direction is captured in the first x-ray image, the image processing apparatus (i) identifies a position of the abdomen in the first x-ray image, (ii) estimates the width of the abdomen based on a profile of the pixel values of each pixel of a pixel row at the position and (iii) estimates the body thickness based on the width.

8. The x-ray image capturing system according to claim 1, wherein the image processing apparatus performs a noise reduction process on a pixel values of the second x-ray image.

9. A body thickness estimation method comprising:
estimating a body thickness of a subject based on signal values generated by an irradiated x-ray image capturing apparatus with no grid attached, the method further comprising:
setting two regions of interest at different parts in a x-ray image captured by the x-ray image capturing apparatus, a second region of interest of the two regions of interest having mainly larger pixel values relative to a first region of interest of the two regions of interest;
creating a histogram from both the signal values of each pixel belonging to the first region of interest and the signal values of each pixel belonging to the second region of interest; and
calculating a characteristic amount from the histogram, the characteristic amount being a difference between two signal values serving as references in a distribution of frequencies on the histogram, wherein
the body thickness is estimated based on the characteristic amount.

* * * * *